United States Patent
Nygaard et al.

(10) Patent No.: US 10,207,297 B2
(45) Date of Patent: Feb. 19, 2019

(54) METHOD AND SYSTEM FOR INSPECTING A MANUFACTURED PART AT AN INSPECTION STATION

(71) Applicant: GII ACQUISITION, LLC, Davisburg, MI (US)

(72) Inventors: Michael G. Nygaard, Fenton, MI (US); James W. St. Onge, Bloomfield Hills, MI (US); Nathan Andrew-Paul Kujacznski, Flint, MI (US); Laura L. Poletti, Grand Blanc, MI (US)

(73) Assignee: GII Inspection, LLC, Davisburg, MI (US)

( * ) Notice: Subject to any disclaimer, the term of this patent is extended or adjusted under 35 U.S.C. 154(b) by 18 days.

(21) Appl. No.: 15/669,079

(22) Filed: Aug. 4, 2017

(65) Prior Publication Data
US 2017/0333953 A1 Nov. 23, 2017

Related U.S. Application Data

(63) Continuation-in-part of application No. 15/501,033, filed as application No. PCT/US2015/034349 on Jun.
(Continued)

(51) Int. Cl.
*G07C 5/08* (2006.01)
*B07C 5/342* (2006.01)
(Continued)

(52) U.S. Cl.
CPC .............. *B07C 5/3422* (2013.01); *B07C 5/08* (2013.01); *G01N 21/8806* (2013.01);
(Continued)

(58) Field of Classification Search
CPC . B07C 5/3422; B07C 5/08; B07C 2501/0009; G02B 13/143;
(Continued)

(56) References Cited

U.S. PATENT DOCUMENTS

| 2,449,255 A | 9/1948 | Sneckner |
| 2,645,343 A | 7/1953 | Nemir |

(Continued)

FOREIGN PATENT DOCUMENTS

| JP | 2010210315 A | * | 9/2010 |
| WO | 2005022076 A2 | | 3/2005 |
| WO | 2009130062 A1 | | 10/2009 |

OTHER PUBLICATIONS

International Preliminary Report on Patentability and Written Opinion, International application No. PCT/US2015/034349, International filing date Jun. 5, 2015, dated Sep. 15, 2015.
United States Patent and Trademark Office, Non-Final Office Action for U.S. Appl. No. 15/501,033, dated Jun. 26, 2018.
International Search Report and Written Opinion, International application No. PCT/US2015/016307; dated Jun. 3, 2015.
(Continued)

*Primary Examiner* — Dominic J Bologna
(74) *Attorney, Agent, or Firm* — Brooks Kushman P.C.

(57) ABSTRACT

Method and system for inspecting a manufactured part supported on an optically-transparent window of a rotary actuator at an inspection station are provided. The window rotatably supports the part in a generally vertical orientation at which a bottom end surface of the part has a position and orientation for optical inspection. An illuminator is configured to illuminate the bottom end surface of the part through the window with radiant energy to obtain reflected radiation signals which are reflected off the bottom end surface of the part. The reflected radiation signals travel through the window. A lens and detector assembly is configured to form a bottom image from the reflected radiation signals at a bottom imaging location below the window and is configured to detect the bottom image. The window is made of a material which is substantially transparent to the radiant energy and the reflected radiation signals.

26 Claims, 7 Drawing Sheets

Related U.S. Application Data 5, 2015, which is a continuation of application No. 14/449,361, filed on Aug. 1, 2014, now Pat. No. 9,228,957, which is a continuation-in-part of application No. 14/221,410, filed on Mar. 21, 2014, now Pat. No. 8,993,914, which is a continuation-in-part of application No. 13/901,868, filed on May 24, 2013, now Pat. No. 9,486,840.

(51) Int. Cl.
  G01N 21/84 (2006.01)
  G01N 21/88 (2006.01)
  G02B 13/14 (2006.01)
  G01N 21/952 (2006.01)
  B07C 5/08 (2006.01)

(52) U.S. Cl.
  CPC ......... *G01N 21/952* (2013.01); *G02B 13/143* (2013.01); *B07C 2501/0009* (2013.01); *B65G 2203/0208* (2013.01); *B65G 2203/044* (2013.01); *G01N 2021/845* (2013.01)

(58) Field of Classification Search
  CPC ...... B65G 2203/0208; B65G 2203/044; G01N 2021/845; G01N 21/8806; G01N 21/952
  See application file for complete search history.

(56) References Cited

U.S. PATENT DOCUMENTS

| | | | |
|---|---|---|---|
| 3,411,009 A | 11/1968 | Ford et al. | |
| 3,604,940 A | 9/1971 | Matthews | |
| 3,770,969 A * | 11/1973 | Ansevin | G01N 21/9045 209/526 |
| 3,924,953 A | 12/1975 | Allard | |
| 4,239,969 A | 12/1980 | Haas et al. | |
| 4,259,013 A | 3/1981 | Faxvog | |
| 4,280,624 A | 7/1981 | Ford | |
| 4,306,808 A | 12/1981 | Vander Neut | |
| 4,315,688 A | 2/1982 | Pryor | |
| 4,351,437 A | 9/1982 | Long | |
| 4,488,648 A * | 12/1984 | Claypool | G01N 21/8851 209/526 |
| 4,519,041 A | 5/1985 | Fant | |
| 4,547,674 A | 10/1985 | Pryor et al. | |
| 4,598,998 A | 7/1986 | Kamei et al. | |
| 4,636,635 A | 1/1987 | Kronseder | |
| 4,644,394 A | 2/1987 | Reeves | |
| 4,691,231 A | 9/1987 | Fitzmorris et al. | |
| 4,721,388 A | 1/1988 | Takagi et al. | |
| 4,794,264 A | 12/1988 | Quackenbos | |
| 4,831,251 A | 5/1989 | Hanna | |
| 4,852,983 A | 8/1989 | Fein | |
| 4,869,813 A | 9/1989 | Bailey | |
| 4,906,098 A | 3/1990 | Thomas et al. | |
| 4,908,507 A * | 3/1990 | Imre | G01N 21/90 250/223 B |
| 4,912,318 A | 3/1990 | Kajiura et al. | |
| 4,923,066 A | 5/1990 | Ophir et al. | |
| 4,969,746 A | 11/1990 | McConnell et al. | |
| 4,970,401 A | 11/1990 | Sadeh et al. | |
| 4,983,043 A | 1/1991 | Harding | |
| 5,012,117 A * | 4/1991 | Karafa | G01N 21/952 250/559.16 |
| 5,024,529 A | 6/1991 | Svetkoff et al. | |
| 5,098,031 A | 3/1992 | Hitomi | |
| 5,164,995 A | 11/1992 | Brooks et al. | |
| 5,168,458 A | 12/1992 | Gomes | |
| 5,170,306 A | 12/1992 | Gomes | |
| 5,280,170 A * | 1/1994 | Baldwin | G01N 21/90 250/223 B |
| 5,291,272 A | 3/1994 | Demirsu | |
| 5,305,391 A * | 4/1994 | Gomibuchi | G01N 21/8851 250/223 B |
| 5,405,015 A * | 4/1995 | Bhatia | B07C 5/3408 209/524 |
| 5,383,021 A | 7/1995 | Hanna | |
| 5,431,289 A | 7/1995 | Hoffman | |
| 5,495,337 A | 2/1996 | Goshorn | |
| 5,521,707 A | 5/1996 | Castore et al. | |
| 5,531,316 A | 7/1996 | Savino | |
| 5,546,189 A | 8/1996 | Svetkoff et al. | |
| 5,568,263 A | 10/1996 | Hanna | |
| 5,608,530 A | 3/1997 | Gates | |
| 5,617,209 A | 4/1997 | Svetkoff et al. | |
| 5,646,724 A | 7/1997 | Hershline | |
| 5,659,624 A | 8/1997 | Fazzari | |
| 5,751,833 A | 5/1998 | Blit | |
| 5,815,275 A | 9/1998 | Svetkoff et al. | |
| 5,847,382 A | 12/1998 | Koch et al. | |
| 5,975,710 A | 11/1999 | Luster | |
| 6,038,521 A | 3/2000 | Kanai | |
| 3,046,462 A | 4/2000 | Yokajty et al. | |
| 6,055,329 A | 4/2000 | Mufti | |
| 3,064,756 A | 5/2000 | Beaty | |
| 6,098,031 A | 8/2000 | Svetkoff et al. | |
| 6,122,045 A | 9/2000 | Pike et al. | |
| 6,252,661 B1 | 6/2001 | Hanna | |
| 6,285,034 B1 | 9/2001 | Hanna et al. | |
| 6,289,600 B1 | 9/2001 | Watts | |
| 6,313,948 B1 | 11/2001 | Hanna | |
| 6,542,235 B1 | 4/2003 | Caskey | |
| 6,542,580 B1 | 4/2003 | Carver | |
| 6,888,627 B2 | 5/2005 | Leslie | |
| 6,950,546 B2 | 9/2005 | Chang | |
| 6,959,108 B1 | 10/2005 | Bartelt et al. | |
| 7,065,242 B2 | 6/2006 | Petrov et al. | |
| 7,123,765 B2 | 10/2006 | Carbone et al. | |
| 7,134,544 B1 | 11/2006 | Kilper et al. | |
| 7,173,692 B2 | 2/2007 | Yasuda et al. | |
| 7,312,607 B2 | 12/2007 | Nygaard | |
| RE39,978 E | 1/2008 | Bieman | |
| 7,329,855 B2 | 2/2008 | Katayama et al. | |
| 7,363,817 B2 | 4/2008 | Bond et al. | |
| 7,403,872 B1 | 7/2008 | St. Onge et al. | |
| 7,626,158 B2 * | 12/2009 | Diehr | B07C 5/3408 250/223 B |
| 7,633,046 B2 | 12/2009 | Spalding | |
| 7,633,634 B2 | 12/2009 | Spalding et al. | |
| 7,633,635 B2 | 12/2009 | Nygaard et al. | |
| 7,684,054 B2 | 3/2010 | Crowther | |
| 7,738,088 B2 | 6/2010 | Spalding | |
| 7,738,121 B2 | 6/2010 | Spalding | |
| 7,755,754 B2 | 7/2010 | Spalding | |
| 7,777,900 B2 | 8/2010 | Nygaard et al. | |
| 7,796,278 B2 | 9/2010 | Spalding et al. | |
| 7,812,970 B2 | 10/2010 | Nygaard | |
| 7,920,278 B2 | 4/2011 | Nygaard | |
| 8,004,694 B2 | 8/2011 | Lee et al. | |
| 3,054,460 A1 | 11/2011 | Agapiou et al. | |
| 8,054,460 B2 | 11/2011 | Agapiou et al. | |
| 8,067,722 B2 * | 11/2011 | Akkerman | G01N 21/9036 250/223 B |
| 8,132,802 B2 | 3/2012 | Kolodge et al. | |
| 8,179,434 B2 | 5/2012 | Koval et al. | |
| 8,228,493 B2 | 7/2012 | Yagyu et al. | |
| 8,372,160 B2 | 2/2013 | Wood et al. | |
| 8,390,826 B2 | 3/2013 | Walstra | |
| 8,416,403 B2 | 4/2013 | Nygaard | |
| 8,550,444 B2 | 10/2013 | Nygaard et al. | |
| 8,570,504 B2 | 10/2013 | Nygaard | |
| 8,615,123 B2 | 12/2013 | Dabic | |
| 8,723,068 B2 | 5/2014 | Nygaard | |
| 8,896,844 B2 | 11/2014 | Nygaard et al. | |
| 8,993,914 B2 | 3/2015 | Kujacznski et al. | |
| 9,019,489 B2 | 4/2015 | Nygaard | |
| 9,228,957 B2 | 1/2016 | Kujacznski et al. | |
| 9,266,148 B2 | 2/2016 | Adams | |
| 9,370,799 B2 | 6/2016 | Nygaard et al. | |
| 9,539,619 B2 | 1/2017 | Kujacznski et al. | |
| 2001/0021026 A1 | 9/2001 | Liu | |
| 2001/0048524 A1 * | 12/2001 | Sones | G01N 21/8806 356/239.4 |

(56) References Cited

U.S. PATENT DOCUMENTS

| | | |
|---|---|---|
| 2003/0034227 A1 | 2/2003 | Gerber |
| 2004/0066505 A1 | 4/2004 | Berg et al. |
| 2005/0174567 A1 | 8/2005 | Hanna |
| 2006/0236792 A1 | 10/2006 | Hanna |
| 2007/0193343 A1* | 8/2007 | Liberatore ............ G01N 11/14 73/54.33 |
| 2007/0223009 A1 | 9/2007 | Erfling et al. |
| 2008/0013820 A1 | 1/2008 | Vertoprakhov et al. |
| 2009/0103107 A1 | 4/2009 | Nygaard |
| 2009/0103112 A1 | 4/2009 | Nygaard et al. |
| 2009/0107896 A1* | 4/2009 | Gochar, Jr. ............ B07C 5/3422 209/577 |
| 2010/0084245 A1 | 4/2010 | Gonzalez Alemany et al. |
| 2010/0108577 A1 | 5/2010 | Wang |
| 2010/0201806 A1 | 9/2010 | Lee et al. |
| 2010/0245850 A1 | 9/2010 | Nygaard |
| 2010/0265324 A1* | 10/2010 | Spalding ............... G01B 11/08 348/92 |
| 2011/0005899 A1 | 1/2011 | Grzelak |
| 2012/0105429 A1 | 11/2012 | Nygaard |
| 2012/0285751 A1 | 11/2012 | Turner |
| 2012/0293623 A1 | 11/2012 | Nygaard |
| 2012/0293789 A1 | 11/2012 | Nygaard |
| 2012/0303157 A1 | 11/2012 | Chung |
| 2013/0235371 A1 | 9/2013 | Nygaard et al. |
| 2013/0258046 A1 | 10/2013 | Nygaard |
| 2014/0043610 A1 | 2/2014 | Engel et al. |
| 2014/0063509 A1 | 3/2014 | Nygaard et al. |
| 2014/0168661 A1 | 6/2014 | Nygaard et al. |
| 2015/0308964 A1* | 10/2015 | Schorn ................. G01N 21/90 356/240.1 |

OTHER PUBLICATIONS

Brosed, Francisco Javier et al.; 3D Geometrical Inspection of Complex Geometry Parts Using a Novel Laser Triangulation Sensor and a Robot; Sensors 2011, 11, 9-110; doi:10.3390/s110100090; published Dec. 23, 2010.

Yogeswaran, Arjun; 3D Surface Analysis for the Automated Dtection of Deformations on Automotive Panels; Ottawa-Carleton Institute for Electrical and Computer Engineeeing School for Information Technology and Engineering, University of Ottawa; Apr. 2011.

International Search Report and Written Opinion; International application No. PCT/US14/16662; dated Dec. 8, 2014.

Notice of Allowance and Fee(s) Due; U.S. Appl. No. 14/221,410, dated Dec. 5, 2014.

Notice of Allowance and Fees Due dated Sep. 8, 2015 for U.S. Appl. No. 14/449,361.

Supplemental Notice of Allowability dated Nov. 5, 2015 for U.S. Appl. No. 14/449,361.

Non-Final Office Action dated May 15, 2015 for U.S. Appl. No. 14/449,361.

Notice of Allowance and Fee(s) Due; related U.S. Appl. No. 13/901,868; dated Jul. 28, 2016.

Non-Final Office Action dated May 26, 2016 for U.S. Appl. No. 14/748,319.

Notice of Allowance and Fees Due dated Sep. 16, 2016 for U.S. Appl. No. 14/748,319.

Non-Final Office Action dated Jun. 26, 2018 for U.S. Appl. No. 15/501,033.

International Search Report and Written Opinion, International application No. PCT/US2014/016663; dated May 28, 2014.

* cited by examiner

METHOD AND SYSTEM FOR INSPECTING A MANUFACTURED PART AT AN INSPECTION STATION

CROSS-REFERENCE TO RELATED APPLICATIONS

This application is a continuation-in-part of U.S. patent application filed on Feb. 1, 2017 and having U.S. Ser. No. 15/501,033. That application is a national phase application of PCT/US2015/034349 filed Jun. 5, 2015 which claims priority to U.S. patent application Ser. No. 14/449,361 filed Aug. 1, 2014, now U.S. Pat. No. 9,228,957, issued Jan. 5, 2016, which is a continuation-in-part of U.S. patent application entitled "HIGH-SPEED, HIGH-RESOLUTION, TRIANGULATION-BASED, 3-D METHOD AND SYSTEM FOR INSPECTING MANUFACTURED PARTS AND SORTING THE INSPECTED PARTS" filed on Mar. 21, 2014 and having U.S. Ser. No. 14/221,410, now U.S. Pat. No. 8,993,914, issued Mar. 31, 2015. That application is a continuation-in-part of U.S. patent application entitled "HIGH-SPEED, TRIANGULATION-BASED, 3-D METHOD AND SYSTEM FOR INSPECTING MANUFACTURED PARTS AND SORTING THE INSPECTED PARTS" filed on May 24, 2013 and having U.S. Ser. No. 13/901,868, now U.S. Pat. No. 9,486,840, issued Nov. 8, 2016.

TECHNICAL FIELD

This invention generally relates to non-contact methods and systems for inspecting manufactured parts at a single inspection station.

OVERVIEW

Traditional manual, gauging devices and techniques have been replaced to some extent by automatic inspection methods and systems. However, such automatic inspection methods and systems still have a number of shortcomings associated with them.

Many manufactured parts, such as fasteners and ammunition cartridges and cases develop cracks, splits, or other outer surface defects during the manufacturing process. While parts can be linearly moved along their axes during the inspection process, this adds additional time to the process.

In optical metrology, inter-reflection (i.e., double bounce or secondary reflection) poses a challenge for surface measurement of shiny objects. Due to specular reflections that can occur among concave surfaces or combinations of surfaces positioned near right angles to each other, the true desired laser lines are often obscured by inter-reflection lines. Such obscuration makes it difficult to measure shiny surfaces of complex surface geometry.

Some laser triangulation measuring equipment generally operate by projecting, with a laser beam having a wavelength centered at approximately 830 nm (infrared (IR) radiation), a light spot having a preset spot size onto the surface to be examined, e.g., from a laser projection "gun" that may be mounted normal to the surface being examined. A light detection unit including a lens and a light detecting element or "camera," such as a CCD or CMOS imaging chip or a position sensing device (PSD), e.g., of silicon, at an offset angle to the projection axis may observe the position of the laser spot in its field of view and output a signal describing the angle at which the spot appeared in the field of view. The range to the object can be computed from the angle information when the distance between the laser projection axis and the light detection unit is known. The offset angle between the laser beam and the line of sight of the light detection unit is often referred to as the "triangulation angle." Based on which part of the detector the light reflected from the imaged object impinges, the height or "z-component" of the object at the point at which the light spot impinges upon the object may be determined.

Inspection of defects on and in small arms ammunition cartridges and cases is a vital aspect in the manufacturing process, allowing for maintenance of a high level of quality and reliability in the munitions industry. Standards have been developed and applied by manufacturers for many years to assist in classifying various types of defects. Alternatively, a military standard is used such as that introduced in 1958 by the U.S. Department of Defense, MIL-STD-636. For small arms ammunition calibers up to 0.50, this standard serves to evaluate and illustrate a practical majority of defects assembled as a result of extensive surveys covering all the small arms ammunition manufacturing facilities in the United States.

As explained in the above-noted military standard, a case is counted as a defective because of a split case if the cartridge case shows a definite separation of the metal entirely through the case wall. A case is classified as either a "major" or "critical" defect depending on the location of split.

U.S. Pat. No. 4,923,066 discloses an automatic visual inspection system for small arms ammunition which sorts visual surface flaws at high speed according to established standards which can be tailored to fit specific needs.

U.S. Pat. No. 7,403,872 discloses a method and system for inspecting manufactured parts such as cartridges and cartridge cases and sorting the inspected parts.

WO 2005/022076 discloses a plurality of light line generators which generate associated beams of light that intersect a part to be inspected.

U.S. Pat. No. 6,313,948 discloses an optical beam shaper for production of a uniform sheet of light for use in a parts inspection system having a light source including a coherent light generator, a diffractive beam shaper, and lens elements.

U.S. Pat. No. 6,285,034 discloses an inspection system for evaluating rotationally asymmetric workpieces for conformance to configuration criteria.

U.S. Pat. No. 6,252,661 discloses an inspection system for evaluating workpieces for conformance to configuration criteria.

U.S. Pat. No. 6,959,108 discloses an inspection system wherein workpieces to be inspected are consecutively and automatically launched to pass unsupported through the field of view of a plurality of cameras.

U.S. Pat. No. 4,831,251 discloses an optical device for discriminating threaded workpiece by the handedness by their screw thread profiles.

U.S. Pat. No. 5,383,021 discloses a non-contact inspection system capable of evaluating spatial form parameters of a workpiece to provide inspection of parts in production.

U.S. Pat. No. 5,568,263 also discloses a non-contact inspection system capable of evaluating spatial form parameters of a workpiece to provide inspection of parts in production.

U.S. Pat. No. 4,852,983 discloses an optical system which simulates the optical effect of traveling over a large distance on light traveling between reference surfaces.

U.S. Patent Application Publication No. 2005/0174567 discloses a system to determine the presence of cracks in parts.

U.S. Patent Application Publication No. 2006/0236792 discloses an inspection station for a workpiece including a conveyor, a mechanism for rotating the workpiece, and a probe.

U.S. Pat. No. 6,289,600 discloses a non-contact measuring device for determining the dimensions of a cylindrical object, such as a pipe.

U.S. Pat. No. 5,521,707 discloses a non-contact, laser-based sensor guided by a precision mechanical system to scan a thread form producing a set of digitized images of the thread form.

WO 2009/130062 discloses a method and a device for the optical viewing of objects.

As described in U.S. Pat. No. 6,098,031, triangulation is the most commonly used 3-D imaging method and offers a good figure of merit for resolution and speed. U.S. Pat. Nos. 5,024,529 and 5,546,189 describe the use of triangulation based systems for inspection of many industrial parts, including shiny surfaces like pins of a grid array. U.S. Pat. No. 5,617,209 shows a scanning method for grid arrays which has additional benefits for improving accuracy. The method of using an angled beam of radiant energy can be used for triangulation, confocal or general line scan systems. Unfortunately, triangulation systems are not immune to fundamental limitations like occlusion and sensitivity to background reflection. Furthermore, at high magnification, the depth of focus can limit performance of systems, particularly edge location accuracy, when the object has substantial relief and a wide dynamic range (i.e. variation in surface reflectance). In some cases, camera-based systems have been combined with triangulation systems to enhance measurement capability.

U.S. Pat. No. 5,098,031 discloses a method and system for high-speed, 3-D imaging of microscopic targets. The system includes confocal and triangulation-based scanners or subsystems which provide data which is both acquired and processed under the control of a control algorithm to obtain information such as dimensional information about the microscopic targets which may be "non-cooperative." The "non-cooperative" targets are illuminated with a scanning beam of electromagnetic radiation such as laser light incident from a first direction. A confocal detector of the electromagnetic radiation is placed at a first location for receiving reflected radiation which is substantially optically collinear with the incident beam of electromagnetic radiation. The triangulation-based subsystem also includes a detector of electromagnetic radiation which is placed at a second location which is non-collinear with respect to the incident beam. Digital data is derived from signals produced by the detectors.

U.S. Pat. No. 5,815,275 discloses triangulation-based 3-D imaging using an angled scanning beam of radiant energy.

Published U.S. Patent Applications 2009/0103107 and 2009/0103112 disclose part inspection using a profile inspection subsystem and triangulation.

U.S. Pat. No. 4,547,674 discloses a method and apparatus for inspecting gear geometry via optical triangulation.

U.S. Pat. No. 4,970,401 discloses a non-contact triangulation probe system including a base plate and a first noncontact triangulation probe including a light source mounted on a first movable slide.

U.S. Pat. Nos. 5,168,458 and 5,170,306 disclose methods and systems for gauging threaded fasteners to obtain tri-lobular parameters.

Other U.S. patent documents related to the invention include: U.S. Pat. Nos. 2,449,255; 3,411,009; 3,604,940; 4,280,624; 4,315,688; 4,598,998; 4,636,635; 4,644,394; 4,691,231; 4,852,983; 4,906,098; 4,912,318; 4,923,066; 4,969,746; 5,521,707; 5,608,530; 5,646,724; 5,291,272; 6,055,329; 4,983,043; 3,924,953; 5,164,995; 4,721,388; 4,969,746; 5,012,117; 5,975,710; 6,038,521; 6,122,045; 7,173,692; 7,329,855; 7,738,121; 6,055,329; 7,065,242; 8,723,068; 7,684,054; 8,004,694; 7,403,872; 7,633,635; 7,312,607; 7,777,900; 7,633,046; 7,633,634; 7,738,121; 7,755,754; 7,738,088; 7,796,278; 7,684,054; 8,054,460; 8,132,802; 8,179,434; 8,550,444; 8,570,504; 8,896,844; 8,993,914; 9,019,489; 9,228,957; 9,370,799; 8,372,160; and 9,539,619 and U.S. published patent applications 2004/0066505; 2008/0013820; 2010/0245850; 2010/0201806, 2012/0293623; 2012/0105429; 2012/0293789; 2013/0235371; and 2014/0063509.

U.S. Pat. No. 8,004,694 discloses a system for indirectly measuring geometric dimensions related to openings in apertured exterior surfaces of parts such as ammunition cases based on direct measurements of the parts when fixtured at a measurement station.

Conventional eddy-current sensing involves the excitation of a conducting winding, the primary, with an electric current source of prescribed frequency. This produces a time-varying magnetic field at the same frequency, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

U.S. Pat. Nos. 7,633,635 and 7,403,872 both assigned to the assignee of the present application disclosure the use of eddy current sensing.

Despite the above art, there is still a need for a non-contact method and system for inspecting manufactured parts quickly and with complete coverage.

SUMMARY OF EXAMPLE EMBODIMENTS

An object of at least one embodiment of the present invention is to provide a method and system for inspecting a manufactured part rotatably supported on an optically-transparent window of a rotary actuator to allow quick inspection cycle time and complete inspection coverage.

In carrying out the above object and other objects of at least one embodiment of the present invention, a method of inspecting a manufactured part at an inspection station is provided. The part has an optically reflective bottom end surface. The method includes the steps of providing an electrically-powered, rotary actuator assembly having a transparent window and utilizing the transparent window to rotatably support the part in a generally vertical orientation at the inspection station at which the bottom end surface of the part has a position and orientation for optical inspection. The method also includes illuminating the bottom end surface of the part through the window with radiant energy at the inspection station to obtain reflected radiation signals which are reflected off the bottom end surface of the part and which reflected radiation signals travel through the window. The method further includes forming a bottom image of the illuminated bottom end surface from the reflected radiation signals at a bottom imaging location below the window at the inspection station. The window is made of a material which is substantially transparent to the radiant energy and the reflected radiation signals. The method still further includes detecting the bottom image at the bottom imaging location and processing the detected bottom image to identify the part as having an unacceptable defect. The unacceptable defect indicates a part parameter or property which fails to fall within a range of acceptable values.

The method may further include electrically powering the actuator assembly to rotate the vertically supported part so that the part moves at predetermined angular increments during at least one rotational scan.

The part may have backside and frontside surfaces when vertically supported. The method may include directing a backside beam of collinated radiation at substantially the entire backside surface of the vertically supported part at each of a first plurality of consecutive angular increments of movement. The backside beam may be occluded by the supported part at each of the first plurality of consecutive increments of movement to create a stream of unobstructed portions of the backside beam in rapid succession passing by and not blocked by the vertically supported part.

The method may further include directing a frontside beam of radiation at at least a portion of the entire frontside surface of the vertically supported part at each of a second plurality of consecutive angular increments of movement. The frontside beam may be reflected by the vertically supported part at each of the second plurality of consecutive increments of movement to create a stream of reflected portions of the frontside beam in rapid succession.

The part may have an optically reflective, top end surface opposite the bottom end surface. The method may further include directing a frontside beam of radiation at the top end surface of the vertically supported part to obtain reflected radiation signals which are reflected off the top end surface of the part.

The method may further include forming a top image of the top end surface from the radiation signals reflected off the top end surface at a top imaging location above the window at the inspection station. The method may further include detecting the top image at the top imaging location and processing the detected bottom image to identify the part as having an unacceptable defect.

The actuator assembly may have an aperture wherein the window is a glass or sapphire window mounted over the aperture.

The part may be rotatably supported on the window without the need for a fixture.

The actuator assembly may include an electric motor wherein the method may further include providing a motor controller or driver to controllably supply electrical power to the motor to rotatably drive the window based on a command signal.

The method may further include providing a system controller for providing the command signal to the controller or driver.

The part may be at least partially conductive or semiconductive wherein the method may further include inducing an eddy current in the part and sensing the induced eddy current to obtain electrical signals.

The method may further include processing the electrical signals to identify the part as having a metallurgical defect.

The method may further include projecting focused lines of radiation at the frontside surface of the supported part during the at least one rotational scan to obtain reflected radiation signals and sensing the reflected radiation signals to obtain electrical signals which represent a depth feature of the part.

Further in carrying out the above object and other objects of at least one embodiment of the present invention, a system for inspecting a manufactured part at an inspection station is provided. The part has an optically reflective bottom end surface. The system includes an electrically-powered, rotary actuator assembly having a transparent window to rotatably support the part in a generally vertical orientation at the inspection station at which the bottom end surface of the part has a position and orientation for optical inspection. An illuminator is configured to illuminate the bottom end surface of the part through the window with radiant energy at the inspection station to obtain reflected radiation signals which are reflected off the bottom end surface of the part and which reflected radiation signals travel through the window. A lens and detector assembly is configured to form a bottom image of the illuminated bottom end surface from the reflected radiation signals at a bottom imaging location below the window at the inspection station and is configured to detect the bottom image at the bottom imaging location. The window is made of a material which is substantially transparent to the radiant energy and the reflected radiation signals. At least one processor is configured to process the detected bottom image to identify the part as having an unacceptable defect. The unacceptable defect indicates a part parameter or property which fails to fall within a range of acceptable values. A system controller is coupled to the actuator assembly to control the actuator assembly.

The system may further include a controller or driver configured to electrically power the actuator assembly to rotate the vertically supported part so that the part moves at predetermined angular increments during at least one rotational scan.

The part may have backside and frontside surfaces when vertically supported. The system may further include a backside illumination assembly to direct a backside beam of collinated radiation at substantially the entire backside surface of the vertically supported part at each of a first plurality of consecutive angular increments of movement. The backside beam may be occluded by the supported part at each of the first plurality of consecutive increments of movement to create a stream of unobstructed portions of the backside beam in rapid succession passing by and not blocked by the vertically supported part.

The system may further include a frontside illumination device configured to direct a frontside beam of radiation at at least a portion of the entire frontside surface of the vertically supported part at each of a second plurality of consecutive angular increments of movement. The frontside beam may be reflected by the vertically supported part at each of the second plurality of consecutive increments of movement to create a stream of reflected portions of the frontside beam in rapid succession.

The part may have an optically reflective, top end surface opposite the bottom end surface. The frontside illuminator device may be configured to direct a frontside beam of radiation at the top end surface of the vertically supported part to obtain reflected radiation signals which are reflected off the top end surface of the part.

The system may further include a second lens and detector assembly to image and detect the radiation signals reflected off the top end surface at a top imaging location above the window at the inspection station to obtain electrical signals and at least one processor configured to process the electrical signals to identify the part as having an unacceptable defect.

The actuator assembly may have an aperture wherein the window may be a glass or sapphire window mounted over the aperture.

The part may be rotatably supported on the window without the need for a fixture.

The actuator assembly may include an electric motor wherein the system may further include a motor controller or driver to controllably supply electrical power to the motor to rotatably drive the window based on a command signal.

The system controller may provide the command signal to the controller or driver.

The part may be at least partially conductive or semiconductive. The system may further include an eddy current sensor to induce an eddy current in the part and sense the induced eddy current to obtain electrical signals.

The system may further include at least one processor to process the electrical signals to identify the part as having a metallurgical defect.

The system may further include an optical depth sensor to sense a depth feature of the part.

Other technical advantages will be readily apparent to one skilled in the art from the following figures, descriptions and claims. Moreover, while specific advantages have been enumerated, various embodiments may include all, some or none of the enumerated advantages.

BRIEF DESCRIPTION OF THE DRAWINGS

For a more complete understanding of the present invention, and for further features and advantages thereof, reference is made to the following description taken in conjunction with the accompanying drawings, in which.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 2:
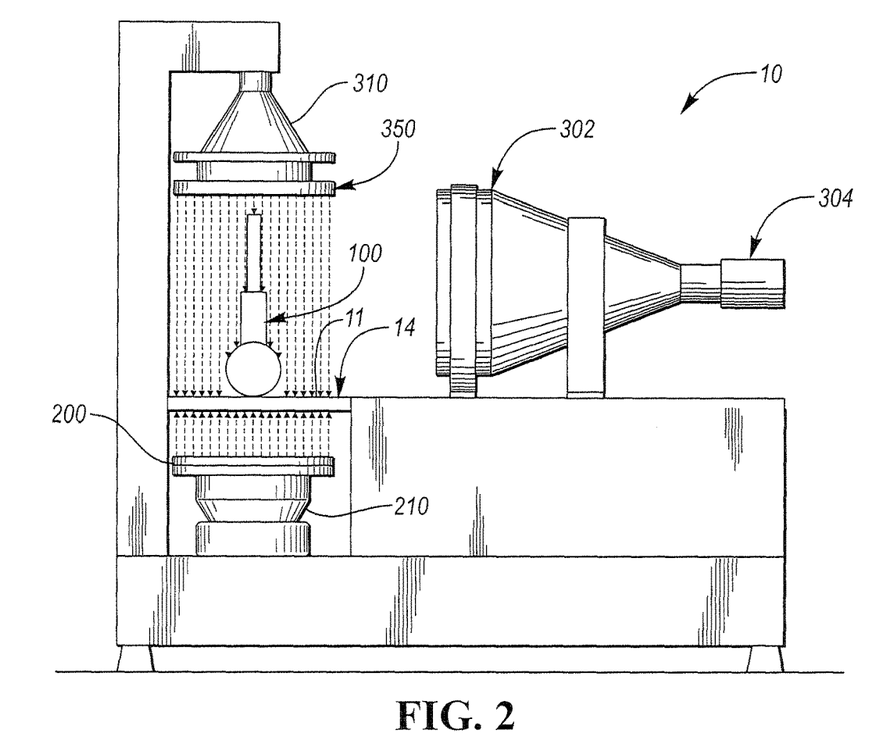
FIG. 2 is a side schematic view of an example embodiment of a system of the present invention including top, side and bottom vision optical components for inspection of a self-supporting part capable of rotating with an optically-transparent window of the system without falling over.
Figure 3:
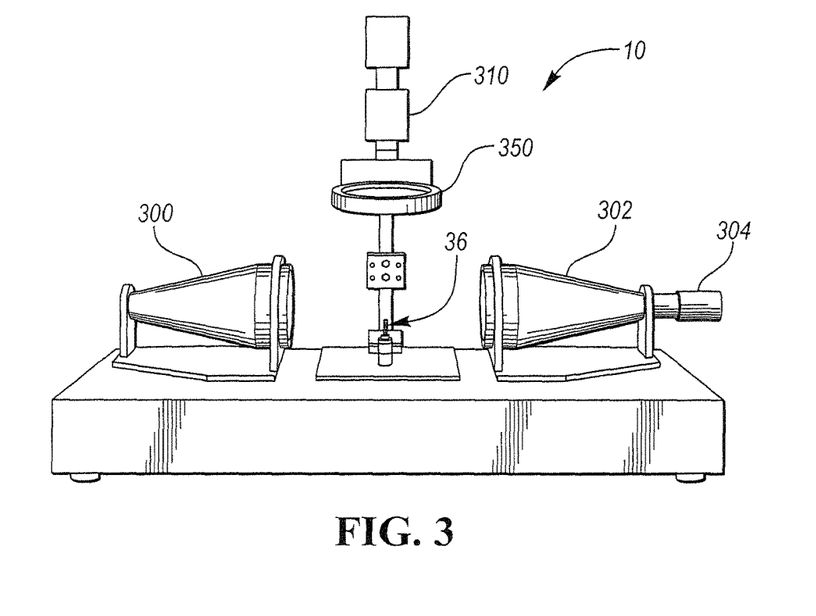
FIG. 3 is a front schematic view of another part and an example embodiment of the system including sequenced front lighting for surface inspection, a high resolution camera and telecentric lens with LED backlighting for profile dimensional inspection; a transparent part stage with motorized rotation with encoder, a bottom LED light source and camera are not included for simplicity.
Figure 4:
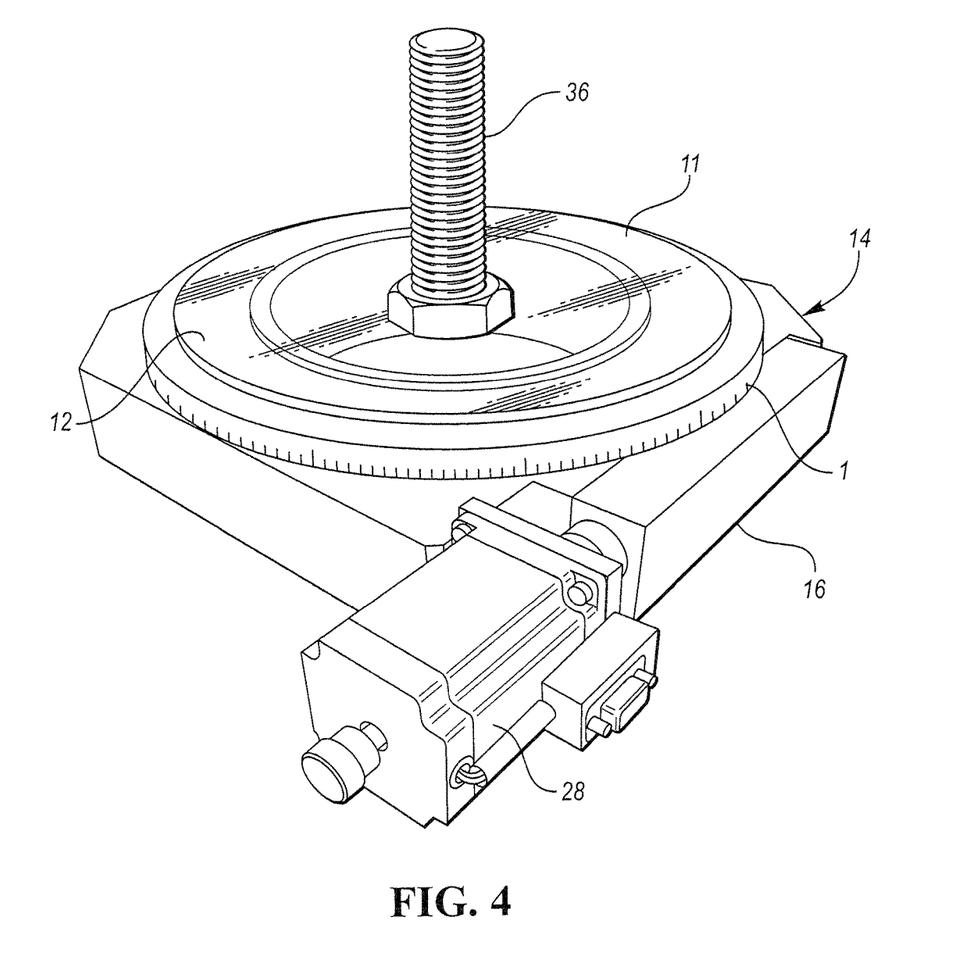
FIG. 4 is a perspective, schematic view of a motorized, rotary or rotation stage having a relatively large central aperture over which a scratch-proof, optically-transparent window is mounted for rotation with an annular plate or slider of the stage.
Figure 5:
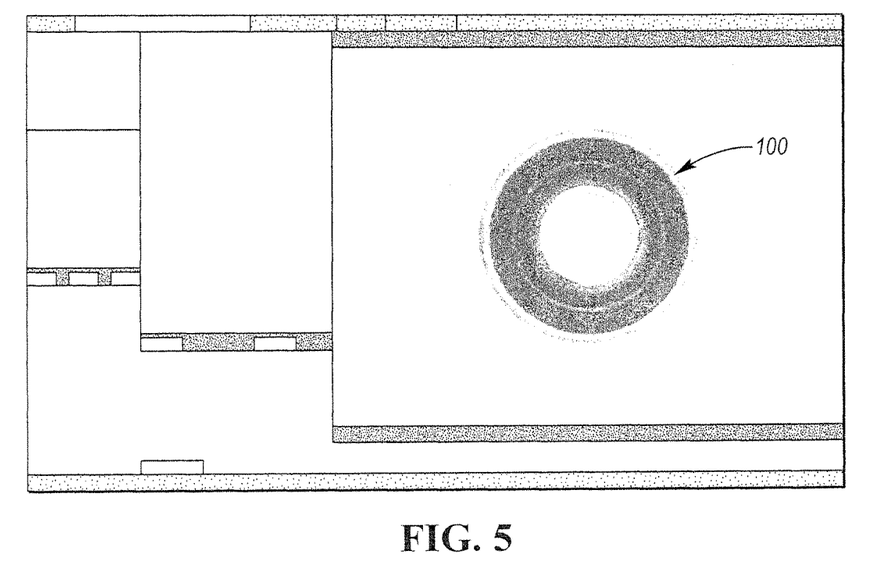
FIG. 5 is a schematic view of a screen shot (without displayed icons or data) from a user interface of a PC which shows top view of the part of FIGS. 1 and 2.
Figure 6:
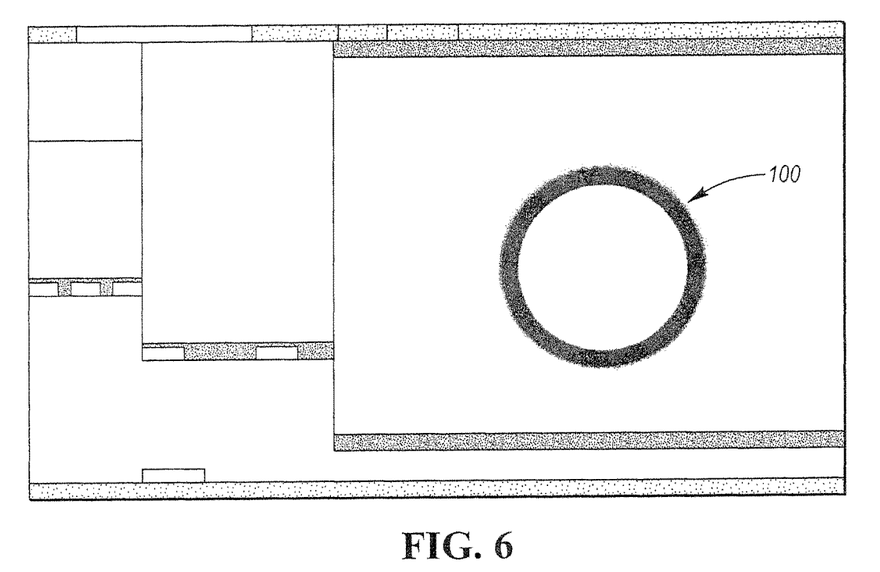
FIG. 6 is a schematic view of another screen shot (again without displayed icons or data) which shows a bottom view of the part of FIGS. 1, 2 and 5.
Figure 7:
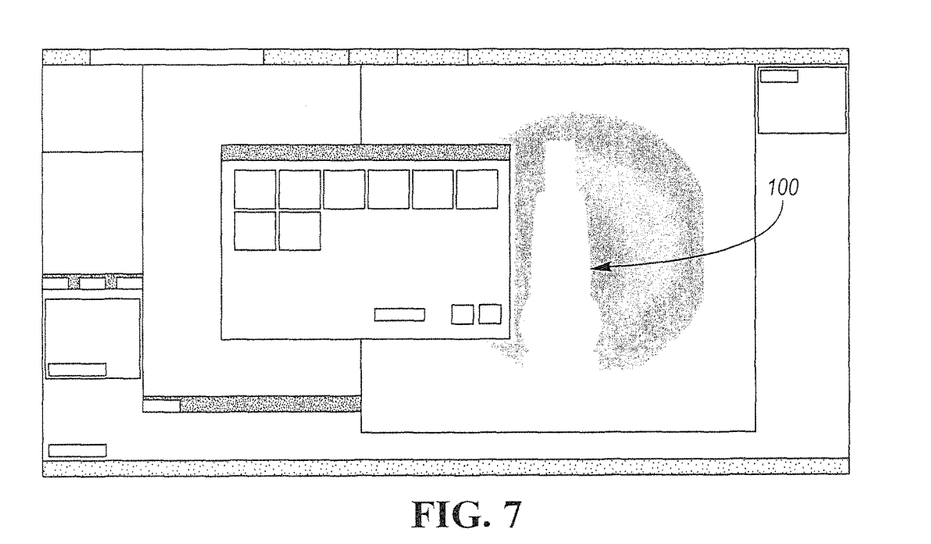
FIG. 7 is a schematic view of yet another screen shot (without displayed icons or data) which shows the part of FIGS. 1, 2, 5 and 6 with backlighting to obtain profile measurements.
Figure 8:
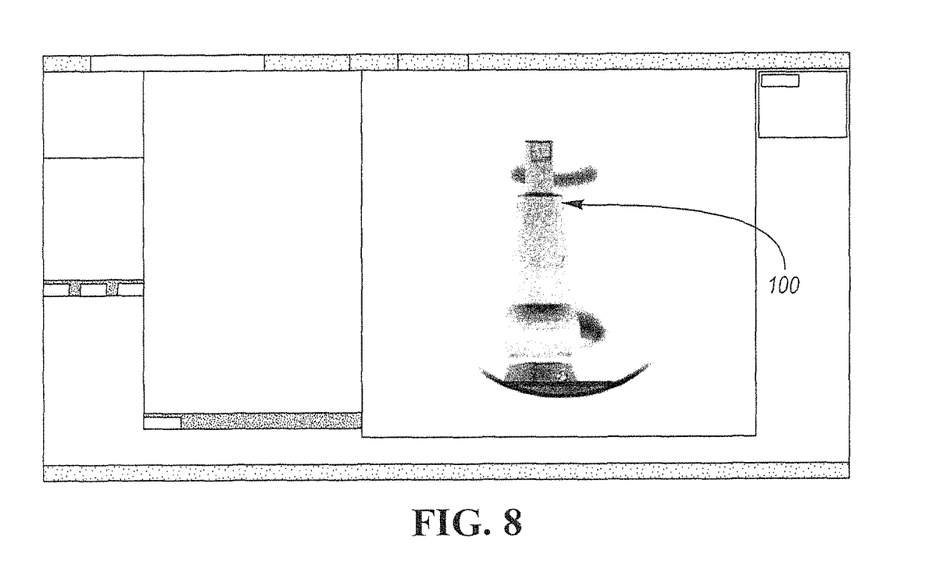
FIG. 8 is a schematic view of still another screen shot (without display icons or data) which shows the part of FIGS. 1, 2, 5, 6 and 7 with lighting to obtain detection of defects such as cracks and other surface inspections.
Figure 9:
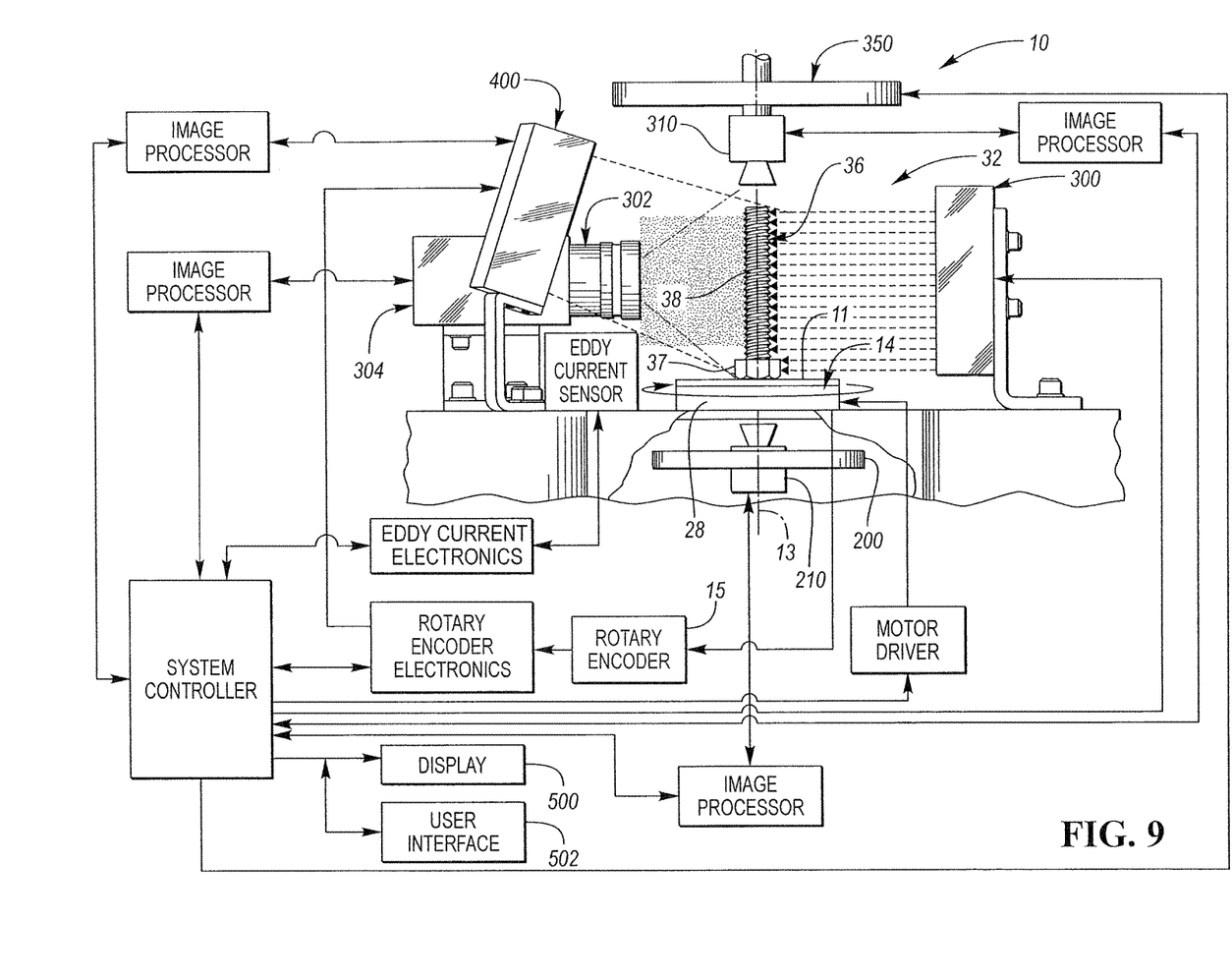
FIG. 9 is a side schematic view, partially broken away, of a system of at least one embodiment of the present invention including the optical inspection devices and actuator assembly of FIGS. 2-4 together with a block diagram of various electronics of the system.
Figure 10:
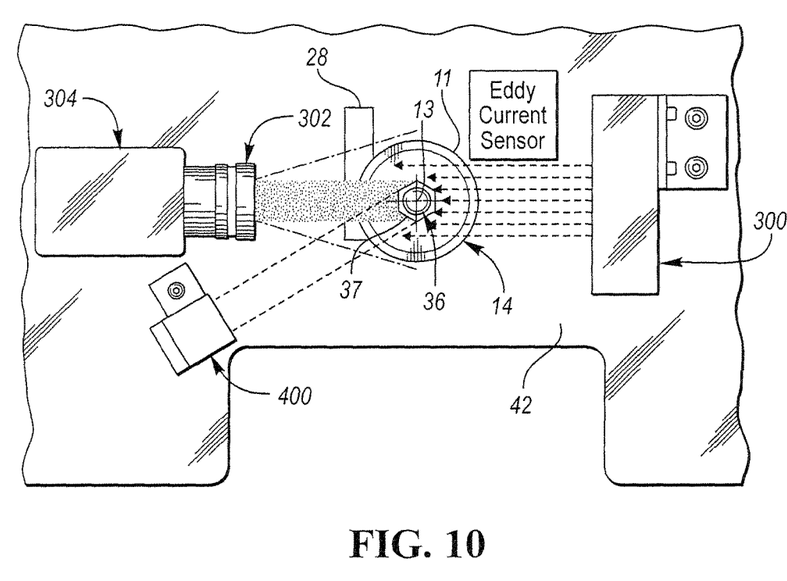
FIG. 10 is a top plan schematic view, partially broken away, of parts and devices of the system of FIGS. 2-4 and 9 including a motorized rotary actuator and an eddy current sensor.

In general, and as described below with reference to FIGS. 2, 3 and 9, at least one embodiment of the present invention provides a non-contact method and system, generally indicated at 10, for inspecting a manufactured part at a single inspection station having a measurement axis 13 (FIGS. 9 and 10). A set of optical inspection devices of a first embodiment of the system is illustrated in FIGS. 2, 3, 9 and 10. Optical inspection devices of the system 10 typically include a high speed, high resolution camera 304, a lens 302, an optical depth sensor 400 (such as a triangulation-based sensor), back lighting 300, front and/or top lighting or illuminator 350, a top camera 310, bottom lighting or illuminator 200 and a bottom camera 210.

Example parts, such as a threaded part 100 with a ball-shaped end portion and a threaded fastener or bolt 36, has threads 38, a length between its ends, a width, and a part axis which, preferably, is central to the part and parallel to its length. A variety of manufactured parts which may be inspected are shown in the drawing figures, including FIG. 1. In one example embodiment, the parts typically have a maximum length of 10", a maximum diameter of 2", a length repeatability of 10 microns, a diameter repeatability of 2 microns, and an inspection speed of about 7 parts per minute. Also, typically, the parts are capable of standing and rotating without falling over (i.e. without the need for a part fixture).

The threaded bolt 36 is held or supported on a transparent (i.e. scratch-proof glass, plastic, or sapphire) window 11 of a motorized rotary or rotation stage, generally indicated at 14 in FIGS. 2, 3, 4, 9 and 10. The part 36 is able to stand on and rotate with the window 11 without falling over without the need for a part fixture.

Because the part 36 is self-supporting on the transparent window 11 without the need for fixtures or other devices, top and bottom cameras and corresponding strobed illuminating LED ring lights are provided to obtain top and bottom end views of the part 36, respectively. The rotation stage 14 may be a precision rotation stage having a relatively large (i.e. 100 mm) central aperture 12 over which the transparent window 11 is fixedly secured to rotate with an annular plate 13 rotatably mounted on a base 16 of the stage 14. An encoder 15 provides an output signal based on the amount of rotary movement of the window 11. Such rotary stages are available from PI micos and may utilize a DC servo motor with a rotary encoder on a rotary shaft of the motor or a stepper motor. A worm drive with a high gear ratio may be provided between the shaft and the annular plate for precision angular positioning of the transparent window and, consequently, the part.

The bottom vision subsystem includes the bottom lighting 200 and the bottom camera 210 both of which are located below the glass window 11 as shown in FIGS. 2 and 9 at a bottom imaging location. The camera 210 is preferably a single view camera with image analysis software that minimizes surface and lighting variations. The lighting 200 illuminates the part.

Detects which the bottom vision subsystem can detect with respect to the part 100:
Min thru-hole
Cracks on flange
Functional OD Hex
Cracks on ball portion
Flange side ID cracks
Top and Bottom ID crack.

The illuminator 200 and the lens and detector subsystem (i.e. camera 210) may be replaced by a high-speed 2D/3D laser scanner available from Keyence Corporation of Japan.

The rotary part stage 14 typically includes an electric actuator or motor 28 which may be a stepper motor or a DC motor.

Figure 1:
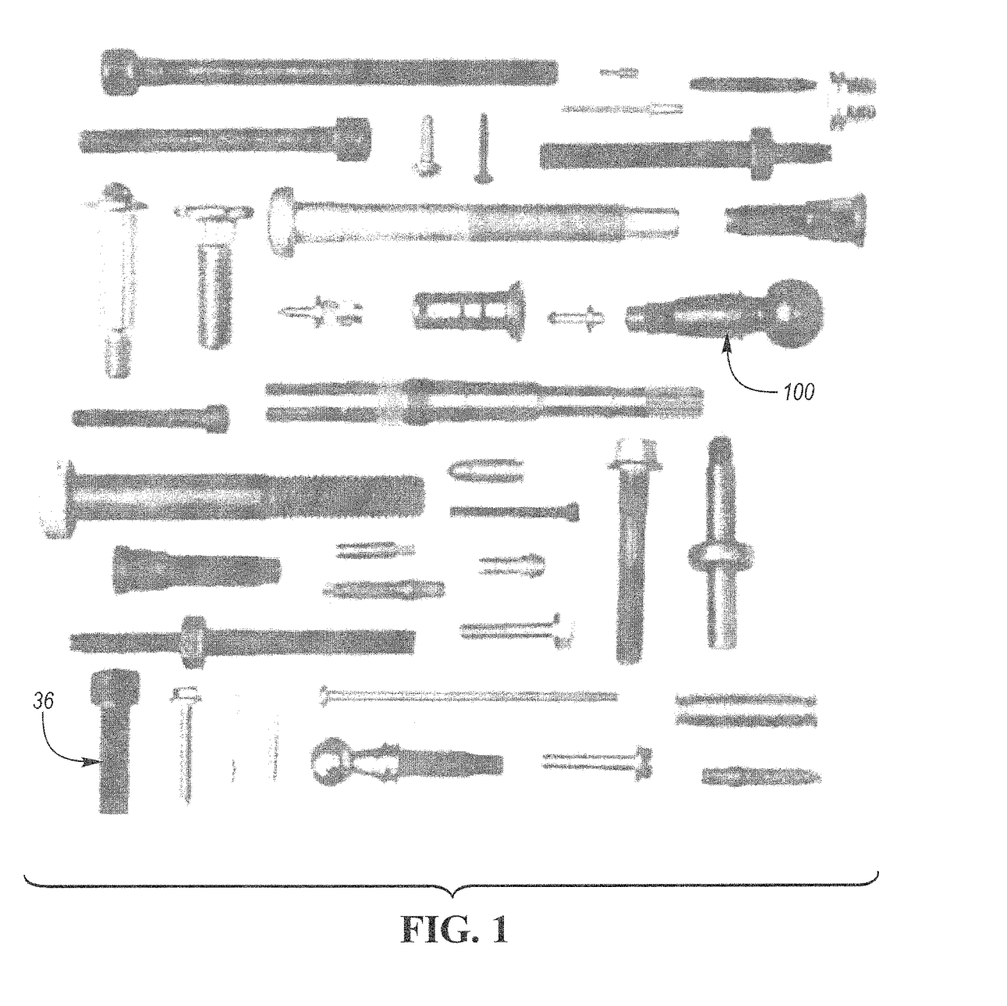
FIG. 1 is a top plan view of various manufactured parts including threaded parts, fasteners and cartridge cases having various symmetric and non-symmetric features and defects which can be extracted and measured using at least one embodiment of the present invention.

The parts of FIG. 1 can be rotatably driven by the motor 28 via a motor driver or controller via a system controller while being supported vertically as shown in FIG. 9.

The system controller typically has a microprocessor, called a central processing unit (CPU), in communication with a memory management unit (MMU). The MMU controls the movement of data among the various computer readable storage media and communicates data to and from the CPU. The computer readable storage media preferably include volatile and nonvolatile storage in read-only memory (ROM), random-access memory (RAM), and keep-alive memory (KAM). For example, KAM may be used to store various operating variables while the CPU is powered down. The computer-readable storage media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by CPU in controlling the various devices of the system 10.

The computer-readable storage media may also include floppy disks, CD-ROMs, hard disks, and the like. CPU communicates with various sensors, switches and/or actuators directly or indirectly via an input/output (I/O) and actuators directly or indirectly via an input/output (I/O) interface or bus. The interface may be implemented as a single integrated interface that provides various raw data or signal conditioning, processing, and/or conversion, short-circuit protection, and the like. Alternatively, one or more dedicated hardware or firmware chips may be used to condition and process particular signals before being supplied to CPU. Some controller architectures do not contain an MMU. If no MMU is employed, the CPU manages data and connects directly to ROM, RAM, and KAM coupled to the MMU or CPU depending upon the particular application.

The various components or functions of the motor driver or controller of FIG. 9 may be implemented by the separate motor controller as illustrated, or may be integrated or incorporated into the system controller, or other controller, depending upon the particular application and implementation. The MCU typically include the control logic to control the rotary stage 14. The control logic may be implemented in hardware, software, or a combination of hardware and software.

One or more memory devices within the system controller and/or the motor controller may store a plurality of activation schemes for the rotatable window 11 and may represent any one or more of a number of known processing strategies such as event-driven, interrupt-driven, multi-tasking, multi-threading, and the like. As such, various steps or functions may be performed in sequence, in a modified sequence, in parallel, or in some cases omitted. Likewise, the order of operation or processing is not necessarily required to achieve the objects, features, and advantages of the invention, but is provided for ease of illustration and description.

Preferably, the control logic is implemented primarily in software executed by a microprocessor-based controller or the microcontroller (i.e. MCU). Of course, the control logic may be implemented in software, hardware, or a combination of software and hardware depending upon the particular application. When implemented in software, the control logic is preferably provided in a computer-readable storage medium having stored data representing instructions executed by a computer to control the angular position and rotation of the window 11 of the system 10 through the rotary stage 14. The computer-readable storage medium or media may be any of a number of known physical devices which utilize electric, magnetic, and/or optical devices to temporarily or persistently store executable instructions and associated calibration information, operating variables, and the like.

In one example embodiment, the plate 13 is electromechanically driven by a rotary actuator such as the DC motor 28 and associated transmission (not shown) in the form of a worm gear or the like. The DC motor may be, for example, a brushed or brushless DC servomotor, the operation of which is controlled by the motor controller via a motor drive or driver within the motor controller. The brushed or brushless motor may have its rotary speed and position controlled by pulse width modulation (PWM) control.

The motor controller outputs motor drive commands to the DC motor based on outputs from the rotary encoder and/or decoded commands from the system controller. The motor controller controls the DC motor through the motor drive of the motor controller so that the angular position of the plate 13 is changed. In other words, the system controller outputs servomotor drive commands to the motor controller which controls the DC motor and, through its transmission, the plate 13.

As described in U.S. Pat. No. 8,550,444 (also owned by the assignee of the present application), the system 10 may include a part-centering and aligning subsystem. The subsystem or apparatus ensures that a part is centered in the system 10 and that the part is aligned with the measurement axis (Z-axis) 13 without the need to measure any distances or angles. In other words, the apparatus ensures that the part is properly placed or positioned on the window 11 in the system 10.

As also described in U.S. Pat. No. 8,550,444, the part-centering apparatus typically includes a carrier which defines a part receiving cavity. The apparatus also has a central axis substantially parallel to the measurement axis 13 or Z-axis and includes a plurality of members or levers having open and closed positions. The members having holding faces which are substantially equidistant from the central axis during movement between the open and closed positions. At least one of the members applies a force on an exterior side surface of a part, disposed between the holding faces during movement between the positions to reposition the part. The repositioned part is centered and aligned with respect to the measurement axis 13. The holding faces releasably hold the repositioned part in the holding position between the open and closed positions of the members.

The part-centering apparatus also typically includes manually operable lever arms which are coupled to their respective relatively moveable, spring-biased ring members of the carrier. Movement of one of the lever arms either towards or away from the other lever arm (depending on the biasing of the spring(s)) causes the members to move from their open position to their holding position against the part to center and align the part.

The system 10 may also include a movable stage subsystem coupled to the part-centering apparatus for sliding the apparatus relative to the repositioned part along the central or measurement axis in the open position of the members to allow the exterior side surface of the repositioned part to be measured. In turn, the slide/base unit moves the movable stage subsystem up and down. A horizontal support member couples the subsystem to the apparatus to move the apparatus along the central or measurement axis.

The system 10 may further include a mechanism which is coupled to one end of the support member for translating the support member and the apparatus a limited extent relative to the subsystem along the central axis. The mechanism includes a manually operable knob to operate the mechanism.

Referring again to FIGS. 3, 9 and 10, the system 10 also includes a backside illumination assembly, generally included at 300. In general, back lighting provides measurement of profile characteristics. This provides maximum, minimum or average measurements, simultaneously or separately for features like: Radii Concentricity, Straightness, Lengths, Diameters and Threads for threaded parts.

The illumination assembly 300 directs a beam of collimated radiation at substantially the entire backside surface of the supported part at predetermined angular increments of movement of the held part about the measurement axis 13 of the system 10 during the rotational scan. The beam is occluded by the held part at each increment of movement to create a stream of unobstructed portions of the beam in rapid succession passing by and not blocked by the held part.

Preferably, substantially the entire backside surface is completely enclosed by a beam profile of the beam. The beam profile is generally rectangular with a height greater than or equal to the length of the part and a width greater than or equal to the width of the part as show in FIGS. 9 and 10.

The assembly 300 may be movable up or down via a motor driven or controlled by a driver/controller upon receiving a control signal from the system controller as shown in U.S. Pat. No. 9,370,799.

The illumination assembly or radiant source 300 illuminates an object such as an ammunition case or threaded bolt to be imaged, and a telecentric optical lens 302 (i.e. FIGS. 2, 3, 9 and 10) receives the radiation passing by and not blocked by the part and guides it towards an image plane of the image acquisition device or detector, generally referred as 304. Consequently, the radiation source 300 preferably comprises a LED emitter including a plurality of LED emitter elements serving to emit radiation in either the visible or ultraviolet range. The LED emitter of the source 300 is preferably high power, capable of generating 100 optical mW or more for each emitting element. A lens (not shown) collimates the radiation.

As shown in U.S. Pat. No. 9,370,799, the back light 300 and the detector 304 may be coupled together by a yoke to rotate together about the part 36 via a motor via a driver/controller upon receiving a command signal from the system controller.

An optical or optoelectronic device for the acquisition of images (for example the camera or telecamera 304) has the image plane which can be, for example, an electronic sensor (CCD, CMOS). The case, bolt or other manufactured part, is received on and retained at a position and orientation for optical inspection by the transparent glass or plastic of the window 11 of the system 10. Preferably the device 304 is a high speed, high resolution digital telecamera, having an electronic sensor with individual pixels of lateral dimensions equal to or less than one or more microns.

As shown in U.S. Pat. No. 9,370,799, the assembly 304 can be driven up and/or down by a motor via a driver/controller upon receiving an appropriate control signal from the system controller. Typically, movement of the assembly 304 and the backlight 300 is coordinated by the system controller so that they move in unison.

As described in U.S. Pat. No. 9,370,799, the lens 302 typically comprises a forward set of optical elements proximal to the manufactured part, a rear optical element proximal to the acquisition device and an aperture diaphragm interposed between the forward and rear sets of optical elements. The aperture diaphragm comprises a circular window transparent to the radiation, which is referred to as a diaphragm aperture. For example, the aperture diaphragm can comprise an opaque plate preferably of thickness of a few tenths of a millimeter, and the diaphragm aperture can be defined a simple hole in the plate.

The diaphragm aperture or window is coaxial to the optical axis of the forward set of optical elements, and positioned on the focal plane of the forward set defined for the wavelength range of radiation emitted by the radiant source.

The position of the focal plane of a set of optical elements mostly depends on the refraction index of the material from which the lenses are made, which, in turn, depends on the wavelength of the electromagnetic radiation passing through the lenses.

The lens 302 only accepts ray cones exhibiting a main (barycentric) axis that is parallel to the optical axis of the forward set. Thereby, the lens 302 is a telecentric lens configured for the particular radiation. The rear set of optical elements serves to compensate and correct the residual chromatic dispersion generated by the forward set optical elements for the wavelength in question.

The optical axis of the rear set coincides with the optical axis of the forward set and the focal plane of the rear set defined for the wavelength cited above, coincides with the plane on which the aperture diaphragm is located. Consequently, rays of radiation conveyed by the rear set towards the image plane form light cones, the main (barycentric) axis of which is parallel to the optical axis of the lens 302.

The forward set preferably includes two positive lenses, which can exhibit a flat-convex, bi-convex, or meniscus shape. The positive lenses can both be made in common optical glass. For example, they can both be made in low chromatic dispersion crown glass.

The rear set of optical elements preferably comprises four lenses. The lens which is proximal to the diaphragm can be a negative lens serving to partially or completely correct the chromatic aberrations generated by the forward set. The negative lens can be bi-concave, flat-concave, or meniscus shaped, and can be made of common optical glass, for example it can be made of high chromatic dispersion flint glass.

The three rear lenses are positive lenses that can all be made of common optical glass, for example in low chromatic dispersion crown glass.

The lens 302 is therefore both telecentric on the object side and telecentric on the image side, and overall the lens 302 is a bi-telecentric lens configured for light such as visible light or ultraviolet light.

Dimensional features that can be measured via the above-described side vision devices include:
 Diameters
 Tapers
 Lengths
 Concentricity
 Straightness
 Parallelism
 Perpendicularity
 Threads
 Pitch
 Major Dia
 Pitch Dia Referring now to FIGS. 9 and 10, there is illustrated a triangulation-based sensor head, generally indicated at 400. The sensor head 400 may comprise a high-speed, 2D/3D laser scanner available from Keyence Corporation of Japan. Such a sensor head from Keyance generates a laser beam that has been expanded into a line and is reflected from the side surface of the part as well as any radially extending surfaces of the part, such as the threaded bolt 36. The reflected line of light is formed on a sensor, and by detecting changes formed on a sensor, and by detecting changes in the position and shape of the reflection, it is possible to measure the position of various points along the surface of the part.

Alternatively, during the scans of the side profile, a laser line may be painted on the part and a vision subsystem positioned on either side of the laser line receives reflected laser light and the resulting images provides a 3D image (including Z axis or depth). In this way, both visual defects and measurement features or characteristics that require a depth component are simultaneously extracted.

Alternatively, (not shown herein but shown in U.S. Pat. No. 9,370,799 the entire disclosure of which is hereby incorporated by reference herein), the sensor head 400 may rotate and/or linearly move via a motor via a rotary driver/controller and/or a linear driver/controller, respectively, upon receiving command signals from the system controller. A transmission may convert the rotary motion of the motor output shaft to linear motion.

As the manufactured part rotates, corresponding sets of 2D profile signals are generated by the sensor head 400. At least one processor processes the sets of 2D profile signals to obtain a 3D view of the complete side and any radially extending surfaces of the part.

The system controller provides control signals based on the signals from the rotary sensor or encoder 15. Alternatively, sensor(s) and/or encoder(s) are not required if stepper motor(s) are provided. Alternatively, or additionally, the signals from the rotary encoder 15 are directly utilized by the sensor head 400 at the station to control the sensor head 400. The control signals are utilized to control the sensor head 400 which preferably have encoder inputs which allow precise control over the position of 2D profile signals samples.

At least one signal processor may process the sets of 2D profile signals to identify a defective part as described in greater detail in U.S. Pat. No. 9,370,799, also owned by the Assignee of the present application. The at least one processor may process the sets of 2D profile signals to obtain one or more measurements of the part.

The operator may tell the system controller via a display 500 and user interface 502 (FIG. 9) where the interesting parameters are located on the Z axis (height of the part). Then, the software tools extract and measure features from the images and resulting 2D profile signals created by the reflected lines of radiation.

The 2D profile signals may be processed by the at least one processor under system control to obtain a 360 degree panoramic composite view or image which is used by the processor to determine at least one of a dent, a split, a perforation, a crack, a scratch, a wrinkle, a buckle, a bulge, and a surface blemish located at the side surfaces of the part where the part is an ammunition case.

A top vision subsystem typically includes the frontside illumination device which may include the strobed ring LED illuminator 350. The illuminator 350 typically includes a curved array of LED light sources, groups of which are under control of the system controller to provide direct illumination of the front of the case or bolt and are used to enhance defects in the front surface of the case or bolt. Alternatively, the frontside illumination device may be side-mounted so that the front light comes from the side of the part and not from above the part, i.e., basically like painting a thin line along the length of the part.

The top vision subsystem also typically includes a single view camera with image analysis software that minimizes surface and lighting variations. Lighting which illuminates the part includes software. The lens of the camera may be up to 2 inches in diameter. The top vision subsystem may detect such defects as castle chip out; functional ID Hex; and top and bottom ID cracks. Front lighting provides surface defect detection for tool chatter, cracks and other surface imperfections.

The detected optical images are processed by the image processor to determine at least one of a dent, a split, a perforation, a crack, a scratch, a wrinkle, a buckle, a bulge, and a surface blemish located at the side surfaces of the case.

Referring to FIGS. 9 and 10, there is illustrated an eddy current sensor which includes coils (not shown) which not only induce an eddy current in the rotating part but also senses the induced eddy current to provide a signal to eddy current electronics which represents the amount of induced eddy current. Typically, the sensed eddy current is compared with an eddy current signature of a "good" part. The eddy current sensor and electronics can be used to inspect for various metallurgical defects such as seams, cracks, porosity, heat treat variations and conductive plating variations.

Data/Image Processor for the Detection of Surface Defects on Small Manufactured Parts.

This vision system is especially designed for the inspection of relatively small manufactured parts (i.e. especially the parts of FIG. 1) which typically have a diameter of 1 mm to 50 mm and a length of up to 228 mm. The processing of images of the cartridge cases and like parts to detect defective cases is generally described in issued U.S. Pat. No. 7,403,872 which also describes the processing of sensed induced eddy current.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of inspecting a manufactured part at an inspection station, the part having an optically reflective bottom end surface, the method comprising the steps of:
    providing an electrically-powered, rotary actuator assembly having a transparent window;
    utilizing the transparent window to rotatably support the part in a generally vertical orientation at the inspection station at which the bottom end surface of the part has a position and orientation for optical inspection;
    illuminating the bottom end surface of the part through the window with radiant energy at the inspection station to obtain reflected radiation signals which are reflected off the bottom end surface of the part and which reflected radiation signals travel through the window;
    forming a bottom image of the illuminated bottom end surface from the reflected radiation signals at a bottom imaging location below the window at the inspection station wherein the window is made of a material which is substantially transparent to the radiant energy and the reflected radiation signals;
    detecting the bottom image at the bottom imaging location; and
    processing the detected bottom image to identify the part as having an unacceptable defect wherein the unacceptable defect indicates a part parameter or property which fails to fall within a range of acceptable values.

2. The method as claimed in claim 1 further comprising:
    electrically powering the actuator assembly to rotate the vertically supported part so that the part moves at predetermined angular increments during at least one rotational scan.

3. The method as described in claim 2, wherein the part has backside and frontside surfaces when vertically supported and wherein the method further comprises directing a backside beam of collinated radiation at substantially the entire backside surface of the vertically supported part at each of a first plurality of consecutive angular increments of movement wherein the backside beam is occluded by the supported part at each of the first plurality of consecutive increments of movement to create a stream of unobstructed portions of the backside beam in rapid succession passing by and not blocked by the vertically supported part.

4. The method as claimed in claim 3 further comprising:
    directing a frontside beam of radiation at at least a portion of the entire frontside surface of the vertically supported part at each of a second plurality of consecutive angular increments of movement, wherein the frontside beam is reflected by the vertically supported part at each of the second plurality of consecutive increments of movement to create a stream of reflected portions of the frontside beam in rapid succession.

5. The method as claimed in claim 3 further comprising projecting focused lines of radiation at the frontside surface of the supported part during the at least one rotational scan to obtain reflected radiation signals and sensing the reflected radiation signals to obtain electrical signals which represent a depth feature of the part.

6. The method as described in claim 1, wherein the part has an optically reflective, top end surface opposite the bottom end surface and wherein the method further comprises directing a frontside beam of radiation at the top end surface of the vertically supported part to obtain reflected radiation signals which are reflected off the top end surface of the part.

7. The method as claimed in claim 6 further comprising:
    forming a top image of the top end surface from the radiation signals reflected off the top end surface at a top imaging location above the window at the inspection station;
    detecting the top image at the top imaging location; and
    processing the detected bottom image to identify the part as having an unacceptable defect.

8. The method as claimed in claim 1, wherein the actuator assembly has an aperture and wherein the window is a glass or sapphire window mounted over the aperture.

9. The method as claimed in claim 1, wherein the part is rotatably supported on the window without the need for a fixture.

10. The method as claimed in claim 1, wherein the actuator assembly includes an electric motor and wherein the method further comprises providing a motor controller or driver to controllably supply electrical power to the motor to rotatably drive the window based on a command signal.

11. The method as claimed in claim 10 further comprising providing a system controller for providing the command signal to the controller or driver.

12. The method as claimed in claim 1, wherein the part is at least partially conductive or semiconductive and wherein the method further comprises inducing an eddy current in the part and sensing the induced eddy current to obtain electrical signals.

13. The method as claimed in claim 12 further comprising processing the electrical signals to identify the part as having a metallurgical defect.

14. A system for inspecting a manufactured part at an inspection station, the part having an optically reflective bottom end surface, the system comprising:
    an electrically-powered, rotary actuator assembly having a transparent window to rotatably support the part in a generally vertical orientation at the inspection station at which the bottom end surface of the part has a position and orientation for optical inspection;
    an illuminator configured to illuminate the bottom end surface of the part through the window with radiant energy at the inspection station to obtain reflected radiation signals which are reflected off the bottom end surface of the part and which reflected radiation signals travel through the window;
    a lens and detector assembly configured to form a bottom image of the illuminated bottom end surface from the reflected radiation signals at a bottom imaging location below the window at the inspection station and configured to detect the bottom image at the bottom imaging location wherein the window is made of a material which is substantially transparent to the radiant energy and the reflected radiation signals;
    at least one processor configured to process the detected bottom image to identify the part as having an unacceptable defect wherein the unacceptable defect indicates a part parameter or property which fails to fall within a range of acceptable values; and
a system controller coupled to the actuator assembly to control the actuator assembly.

15. The system as claimed in claim 14 further comprising:
a controller or driver configured to electrically power the actuator assembly to rotate the vertically supported part so that the part moves at predetermined angular increments during at least one rotational scan.

16. The system as described in claim 15, wherein the part has backside and frontside surfaces when vertically supported and wherein the system further comprises a backside illumination assembly to direct a backside beam of collinated radiation at substantially the entire backside surface of the vertically supported part at each of a first plurality of consecutive angular increments of movement wherein the backside beam is occluded by the supported part at each of the first plurality of consecutive increments of movement to create a stream of unobstructed portions of the backside beam in rapid succession passing by and not blocked by the vertically supported part.

17. The system as claimed in claim 16 further comprising:
a frontside illumination device configured to direct a frontside beam of radiation at at least a portion of the entire frontside surface of the vertically supported part at each of a second plurality of consecutive angular increments of movement, wherein the frontside beam is reflected by the vertically supported part at each of the second plurality of consecutive increments of movement to create a stream of reflected portions of the frontside beam in rapid succession.

18. The system as described in claim 17, wherein the part has an optically reflective, top end surface opposite the bottom end surface and wherein the frontside illuminator device is configured to direct a frontside beam of radiation at the top end surface of the vertically supported part to obtain reflected radiation signals which are reflected off the top end surface of the part.

19. The system as claimed in claim 18 further comprising:
a second lens and detector assembly to image and detect the radiation signals reflected off the top end surface at a top imaging location above the window at the inspection station to obtain electrical signals; and
at least one processor configured to process the electrical signals to identify the part as having an unacceptable defect.

20. The system as claimed in claim 14, wherein the actuator assembly has an aperture and wherein the window is a glass or sapphire window mounted over the aperture.

21. The system as claimed in claim 14, wherein the part is rotatably supported on the window without the need for a fixture.

22. The system as claimed in claim 14, wherein the actuator assembly includes an electric motor and wherein the system further comprises a motor controller or driver to controllably supply electrical power to the motor to rotatably drive the window based on a command signal.

23. The system as claimed in claim 22, wherein the system controller provides the command signal to the controller or driver.

24. The system as claimed in claim 14, wherein the part is at least partially conductive or semiconductive and wherein the system further comprises an eddy current sensor to induce an eddy current in the part and sense the induced eddy current to obtain electrical signals.

25. The system as claimed in claim 24 further comprising at least one processor to process the electrical signals to identify the part as having a metallurgical defect.

26. The system as claimed in claim 14 further comprising an optical depth sensor to sense a depth feature of the part.

* * * * *